(12) United States Patent
Kishida et al.

(10) Patent No.: US 8,226,636 B2
(45) Date of Patent: Jul. 24, 2012

(54) BIOLOGICAL TISSUE BONDING DEVICE AND BIOLOGICAL TISSUE BONDING MEDICAL INSTRUMENT

(75) Inventors: Akio Kishida, Toyko (JP); Toru Masuzawa, Ibaraki (JP); Tetsuya Higami, Hokkaido (JP)

(73) Assignees: National University Corporation Tokyo Medical and Dental University, Tokyo (JP); National University Corporation Ibaraki University, Ibaraki (JP); National University Corporation Shimane University, Shimane (JP)

( * ) Notice: Subject to any disclaimer, the term of this patent is extended or adjusted under 35 U.S.C. 154(b) by 901 days.

(21) Appl. No.: 12/224,498

(22) PCT Filed: Mar. 1, 2007

(86) PCT No.: PCT/JP2007/053969
§ 371 (c)(1),
(2), (4) Date: Nov. 20, 2008

(87) PCT Pub. No.: WO2007/100063
PCT Pub. Date: Sep. 7, 2007

(65) Prior Publication Data
US 2009/0105701 A1   Apr. 23, 2009

(30) Foreign Application Priority Data
Mar. 1, 2006 (JP) ................................ 2006-055619
Mar. 1, 2006 (JP) ................................ 2006-055620

(51) Int. Cl.
*A61B 18/04* (2006.01)

(52) U.S. Cl. ................ 606/27; 606/28; 606/29; 606/30; 606/31

(58) Field of Classification Search ............. 606/27–28, 606/29–31, 277, 169, 75, 139, 151, 324; 600/37; 128/897–898
See application file for complete search history.

(56) References Cited

U.S. PATENT DOCUMENTS
5,989,248 A * 11/1999 Tu et al. ....................... 606/41
6,355,032 B1 * 3/2002 Hovda et al. .................. 606/32

FOREIGN PATENT DOCUMENTS
JP   A-63-292951   11/1988
(Continued)

OTHER PUBLICATIONS
PCT International Search Report mailed on Apr. 17, 2007 for the corresponding International patent application No. PCT/JP2007/053969.
Written Reply dated Dec. 28, 2007 in corresponding International Application No. PCT/JP2007/053969.
(Continued)

*Primary Examiner* — Bhisma Mehta
*Assistant Examiner* — Edelmira Bosques
(74) *Attorney, Agent, or Firm* — Posz Law Group, PLC

(57) ABSTRACT

A device 1*a* for bonding adherends T1 and T2, as a device for bonding biological tissue to biological tissue or a biological tissue bonding material, comprises: a clamping part 2*a* for clamping the adherends T1 and T2 between members 21*a* and 22*a*; a pressing part 3*a* for pressing the member 22*a* towards the member 21*a*; a pressure control part 4*a* for controlling the pressure by the pressing part 3*a*; a heating element 5*a* built into the member 21*a*; a heating control part 6*a* for controlling the heating by the heating element 5*a*; a vibration generating part 7*a* for generating microvibration; and a vibration control part 8*a* for controlling the microvibration generated by the vibration generating part 7*a*.

16 Claims, 6 Drawing Sheets

FOREIGN PATENT DOCUMENTS

| | | |
|---|---|---|
| JP | A-2002-540822 | 12/2002 |
| JP | A-2003-111771 | 4/2003 |
| JP | A-2004-97007 | 4/2004 |
| JP | A-2005-066316 | 3/2005 |

OTHER PUBLICATIONS

Kagaku Daijiten, Encyclopedia Chimica, p. 736 (partial translation), submitted with the Written Reply dated Dec. 28, 2007.

* cited by examiner (c) WET COLLAGEN (b) VINYLON (a) POLYURETHANE

POLYURETHANE-COATED STAINLESS STEEL PIECE

POLYURETHANE-COATED POLYESTER PIECE

BIOLOGICAL TISSUE BONDING DEVICE AND BIOLOGICAL TISSUE BONDING MEDICAL INSTRUMENT

CROSS REFERENCE TO RELATED APPLICATIONS

This application is a U.S. national stage application of PCT/JP2007/053969 filed on Mar. 1, 2007, and claims priority to, and incorporates by reference, Japanese Patent Application Nos. 2006-055619 and 2006-055620 filed on Mar. 1, 2006.

TECHNICAL FIELD

The present invention relates to a device for bonding biological tissue to biological tissue or to a biological tissue bonding material, and relates to a medical instrument capable of bonding to biological tissue

BACKGROUND

Conventionally, suture thread, adhesives, automatic anastomotic devices, staplers, clips or the like have been used to bond biological tissues together. However, suture thread is problematic in that, for instance, it takes time (in particular, fine sutures) and requires skill. Adhesives (for instance, fibrin pastes, cyanoacrylate or the like) are problematic, for instance, on account of low bonding strength and low safety (for instance, infectiveness in fibrin pastes and carcinogenicity in cyanoacrylate). Automatic anastomotic devices are difficult to employ in small sites, which is problematic, while staplers, clips or the like are problematic in that they require a long time for bonding.

Meanwhile, biological tissues can be coagulated/bonded to one another by using ultrasonic scalpels (vibration mode), but these scalpels require a horn for obtaining large vibration amplitudes, which makes device miniaturization difficult. Also, it is thought that bonding between biological tissues by ultrasonic scalpel arises from a partial fusion of the collagen matrix in the biological tissue, on account of the friction heat generated by the ultrasonic vibration of the scalpel blade. High-frequency scalpels allow bonding biological tissues together through heating (about 100° C.) brought about by the high frequency, but may inflict damage on the surroundings owing to the large size of the scalpel portion. Electrocautery scalpels (hemostasis mode) allow arresting hemorrhages by burning away biological tissue at a high temperature (300° C.), but it is difficult to bond biological tissues together using such electrocautery scalpels.

Meanwhile, angioplasty by way of stents is used for the therapy of stenosis in patients whose blood vessels are partially stenotic. Stent-graft implantation is performed for treating aortic aneurysm in patients whose aorta expands partially. Therapies using stents and stent-grafts involve extremely low-invasive procedures, since they require no thoracotomy, as is the case in artificial blood vessel replacement.

However, stents and stent-grafts are not sutured, and hence there may occur problems such as leakage of blood into the aneurysm on account of imperfect bonding with the artery (endoleaks), or drifting away from the implant site through the action of blood flow.

DISCLOSURE OF THE INVENTION

Problem to be Solved by the Invention

An object of the present invention is to provide a device for bonding biological tissue to biological tissue or to a biological tissue bonding material.

A further object of the present invention is to provide a medical instrument (for instance, a stent, stent graft or the like) that can be solidly bonded to biological tissue (for instance, blood vessels or the like).

Means for Solving the Problem

In order to solve the above problems, a first device of the present invention is a device for bonding biological tissue, as a first adherend, and biological tissue or a biological tissue bonding material, as a second adherend, the device comprising: a clamping part for clamping the first and second adherends in such a manner that the first and second adherends are in contact with each other; a clamping force control part for controlling the clamping force of the clamping part in such a manner that the pressure exerted on the first and second adherends clamped by the clamping part is $9 \times 10^2$ to $1 \times 10^5$ $N/m^2$; a heating part for heating the first and/or second adherend clamped by the clamping part; a heating control part for controlling the heating by the heating part in such a manner that the temperature of the first and second adherends clamped by the clamping part is 60 to 140° C.; a vibration part for imparting vibration to the first and/or second adherend clamped by the clamping part; and a vibration control part for controlling the vibration imparted by the vibration part in such a manner that the first and second adherends clamped by the clamping part vibrate with a frequency of 1 to 100 kHz.

In the first device of the present invention, the clamping part clamps the first and second adherends in contact with each other.

In the first device of the present invention, the clamping force of the clamping part is controlled by the clamping force control part in such a manner that the pressure exerted on the first and second adherends clamped by the clamping part ranges from $9 \times 10^2$ to $1 \times 10^5$ $N/m^2$.

In the first device of the present invention, the heating control part controls the heat generated by the heating part in such a manner that the first and second adherends clamped by the clamping part are heated at 60 to 140° C. The heating part heats one or both of the first and second adherends, but since the first and second adherends are in contact with each other, the heat applied to one of the adherends is transmitted to the other adherend, whereby the latter becomes heated as well.

In the first device of the present invention, the vibration control part controls the vibration of the vibration part in such a manner that the first and second adherends clamped by the clamping part vibrate with a frequency ranging from 1 to 100 kHz. The vibration part imparts vibration to one or both of the first and second adherends, but since the first and second adherends are in contact with each other, the vibration imparted to one of the adherends is transmitted to the other adherend, whereby the other adherend becomes vibrated as well. The direction of the vibration imparted to the first and second adherends is not particularly limited. For instance, the direction of the vibration can be substantially parallel to the contact surface of the first and second adherends, or substantially perpendicular to the contact surface of the first and second adherends.

In the first device of the present invention, therefore, the clamping part clamps the first and second adherends in contact with each other, whereupon the first and second adherends are subjected to a pressure of $9 \times 10^2$ to $1 \times 10^5$ $N/m^2$, to a temperature of 60 to 140° C. and to vibration of frequency ranging from 1 to 100 kHz. Thereby, the first and second adherends become bonded solidly and quickly. When the first and second adherends are subjected to the above-described pressure, temperature and vibration, the damage inflicted on the first and second adherends is small. Preferably, the pressure applied to the first and second adherends ranges from $1 \times 10^4$ to $5 \times 10^4$ N/m$^2$, the temperature ranges from 80 to 110° C. and the frequency of the vibration ranges from 10 to 60 kHz.

In the first device of the present invention, preferably, the vibration control part controls the vibration imparted by the vibration part in such a manner that the first and second adherends clamped by the clamping part vibrate with an amplitude smaller than 100 μm.

The amplitude of the vibration imparted to the first and second adherends is not particularly limited, provided that the first and second adherends are subjected to a pressure of $9 \times 10^2$ to $1 \times 10^5$ N/m$^2$, a temperature of 60 to 140° C. and a vibration of frequency ranging from 1 to 100 kHz. To obtain an amplitude of 100 μm or greater, however, large vibrators, horns or the like are required, and thus it is difficult to reduce device size. In the first device of the present invention, by contrast, a small vibrator can be used and no horn need be provided, when the first and second adherends clamped by the clamping part vibrate with an amplitude smaller than 100 μm. This allows reducing as a result the size of the device. By reducing the size of the device, the device can be used in endoscopic surgery, endovascular therapy and the like.

The constitution of the first device of the present invention can be appropriately modified in accordance with, for instance, the thickness of the first and second adherends. The thickness of the first and second adherends denotes the thickness in the direction perpendicular to the contact surface of the first and second adherends.

In the first device of the present invention, for instance, the clamping part clamps the first and second adherends between a first contact part that is in contact with the first adherend and a second contact part that is in contact with the second adherend; the heating part heats the first and/or second adherend clamped by the clamping part by heating the first and/or second contact part; and the vibration part imparts vibration to the first and/or second adherend clamped by the clamping part by imparting vibration to the first and/or second contact part. In this case, to facilitate application of a pressure of $9 \times 10^2$ to $1 \times 10^5$ N/m$^2$, a temperature of 60 to 140° C. and vibration of frequency ranging from 1 to 100 kHz at the portions of the first and second adherends that are in contact with each other, the thickness of the first and second adherends is preferably small. The thickness of the first and second adherends ranges ordinarily from 0.01 to 5 mm, preferably from 0.1 to 1 mm.

The first device of the present invention comprises, for instance, an interposing part that can be interposed between the first and second adherends, with the first and second adherend in contact with each other, wherein the heating part heats the first and/or second adherend clamped by the clamping part by heating the intercalated part; and the vibration part imparts vibration to the first and/or second adherend clamped by the clamping part by imparting vibration to the interposing part. In this case, a pressure of $9 \times 10^2$ to $1 \times 10^5$ N/m$^2$, a temperature of 60 to 140° C. and vibration of frequency ranging from 1 to 100 kHz can be easily applied to the portions of the first and second adherends that are in contact with each other, and hence the first and second adherends can be made thicker. The thickness of the first and second adherends ranges ordinarily from 0.01 to 10 mm, preferably from 0.1 to 5 mm.

In order to solve the above problems, the second device of the present invention is a device for bonding biological tissue, as a first adherend, and biological tissue or a biological bonding material, as a second adherend, the device comprising: a pressing part for pressing one of the first and second adherends towards the other one of the adherends; a pressure control part for controlling the pressure of the pressing part in such a manner that the pressure exerted on the first and second adherends is $9 \times 10^2$ to $1 \times 10^5$ N/m$^2$; a heating part for heating the first and/or second adherend; a heating control part for controlling the heating by the heating part in such a manner that the temperature of the first and second adherends is 60 to 140° C.; a vibration part for imparting vibration to the first and/or second adherend; and a vibration control part for controlling the vibration imparted by the vibration part in such a manner that the first and second adherends vibrate with a frequency of 1 to 100 kHz.

In the second device of the present invention, the pressing part presses one of the first and second adherends towards the other one of the adherends, to bring thereby the first and second adherends into contact with each other.

In the second device of the present invention, the pressure control part controls the pressure of the pressing part so that the pressure exerted on the first and second adherends ranges from $9 \times 10^2$ to $1 \times 10^5$ N/m$^2$. To allow pressure to be applied to the first and second adherends, as a reaction upon being pressed by one of the adherends against the other adherend, the other adherend has to push back against one of the adherends. As the other adherend, therefore, there is selected an adherend capable of exerting such a reaction (for instance, tissue fixed to a living body such as a blood vessel or the like).

In the second device of the present invention, the heating control part controls the heat generated by the heating part in such a manner that the first and second adherends are heated at 60 to 140° C. The heating part heats one or both of the first and second adherends, but since the first and second adherends are in contact with each other, the heat applied to one of the adherends is transmitted to the other adherend, whereby the other adherend becomes heated as well.

In the second device of the present invention, the vibration control part controls the vibration of the vibration part in such a manner that the first and second adherends vibrate with a frequency ranging from 1 to 100 kHz. The vibration part imparts vibration to one or both of the first and second adherends, but since the first and second adherends are in contact with each other, the vibration imparted to one of the adherends is transmitted to the other adherend, whereby the other adherend becomes vibrated as well. The direction of the vibration imparted to the first and second adherends is not particularly limited. For instance, the direction of the vibration can be substantially parallel to the contact surface of the first and second adherends, or substantially perpendicular to the contact surface of the first and second adherends.

In the second device of the present invention, therefore, the first and second adherends are in contact with each other, whereupon the first and second adherends are subjected to a pressure of $9 \times 10^2$ to $1 \times 10^5$ N/m$^2$, to a temperature of 60 to 140° C. and to vibration of frequency ranging from 1 to 100 kHz. Thereby, the first and second adherends become bonded solidly and quickly. When the first and second adherends are subjected to the above-described pressure, temperature and vibration, the damage inflicted on the first and second adherends is small. Preferably, the pressure applied to the first and second adherends ranges from $1 \times 10^4$ to $5 \times 10^4$ N/m$^2$, the temperature ranges from 80 to 110° C. and the frequency of the vibration ranges from 10 to 60 kHz.

In the second device of the present invention, preferably, the vibration control part controls the vibration of the vibration part in such a manner that the first and second adherends vibrate with an amplitude smaller than 100 μm.

The amplitude of the vibration imparted to the first and second adherends is not particularly limited, provided that the first and second adherends are subjected to a pressure of $9 \times 10^2$ to $1 \times 10^5 \text{N/m}^2$, a temperature of 60 to 140° C. and a vibration of frequency ranging from 1 to 100 kHz. In the second device of the present invention, small vibrators can be used and no horn need be provided, when the first and second adherends vibrate with an amplitude smaller than 100 μm. This allows reducing as a result the size of the device. By reducing the size of the device, the device can be used in endoscopic surgery, endovascular therapy and the like.

The second device of the present invention comprises, for instance, a contact part that is in contact with the first or second adherend, wherein the heating part heats the first or second adherend by heating the contact part, and the vibration part imparts vibration to the first or second adherend by imparting vibration to the contact part. To reliably contact herein the first or second adherend with the contact part, the pressing part preferably presses one of the first and second adherends towards the other adherend by pressing the contact part towards one of the first and second adherends. The pressing part, thus, presses the contact part towards one of the first and second adherends, to allow thereby reliably contacting the contact part to one of the first and second adherends.

In order to solve the above problems, the present invention provides also a medical instrument having on the surface thereof a portion comprising a biological tissue bonding material, wherein the biological tissue bonding material is a material that can be bonded to biological tissue by, when in contact with the biological tissue, being subjected to a pressure of $9 \times 10^2$ to $1 \times 10^5$ N/m$^2$, to a temperature of 60 to 140° C., and to vibration of frequency ranging from 1 to 100 kHz.

In the medical instrument of the present invention, preferably, the biological tissue bonding material is wet collagen, polyurethane, vinylon, gelatin, or a composite material thereof.

In the medical instrument of the present invention, the medical instrument is, for instance, a stent or a stent-graft.

A biological tissue bonding material and biological tissue are thus solidly and quickly bonded together by applying to the biological tissue bonding material and the biological tissue, while in contact with each other, a pressure of $9 \times 10^2$ to $1 \times 10^5$ N/m$^2$, a temperature of 60 to 140° C. and vibration of frequency ranging from 1 to 100 kHz. When the biological tissue bonding material and the biological tissue are subjected to the above-described pressure, temperature and vibration, the damage inflicted on the biological tissue bonding material and the biological tissue is small. Preferably, the pressure applied to the biological tissue bonding material and the biological tissue ranges from $1 \times 10^4$ to $5 \times 10^4$ N/m$^2$, the temperature ranges from 80 to 110° C. and the frequency of the vibration ranges from 10 to 60 kHz.

Advantageous Effect of the Invention

The present invention provides a device for bonding biological tissue to biological tissue or to a biological tissue bonding material. The device of the present invention can be used in, for instance, endoscopic surgery, endovascular therapy or the like by being combined with surgical tweezers, clips at the tip of endoscope, vascular catheters or the like.

The present invention provides also a medical instrument (for instance, a stent, stent-graft or the like) that can be solidly bonded to biological tissue (for instance, blood vessels or the like).

Figure 1:
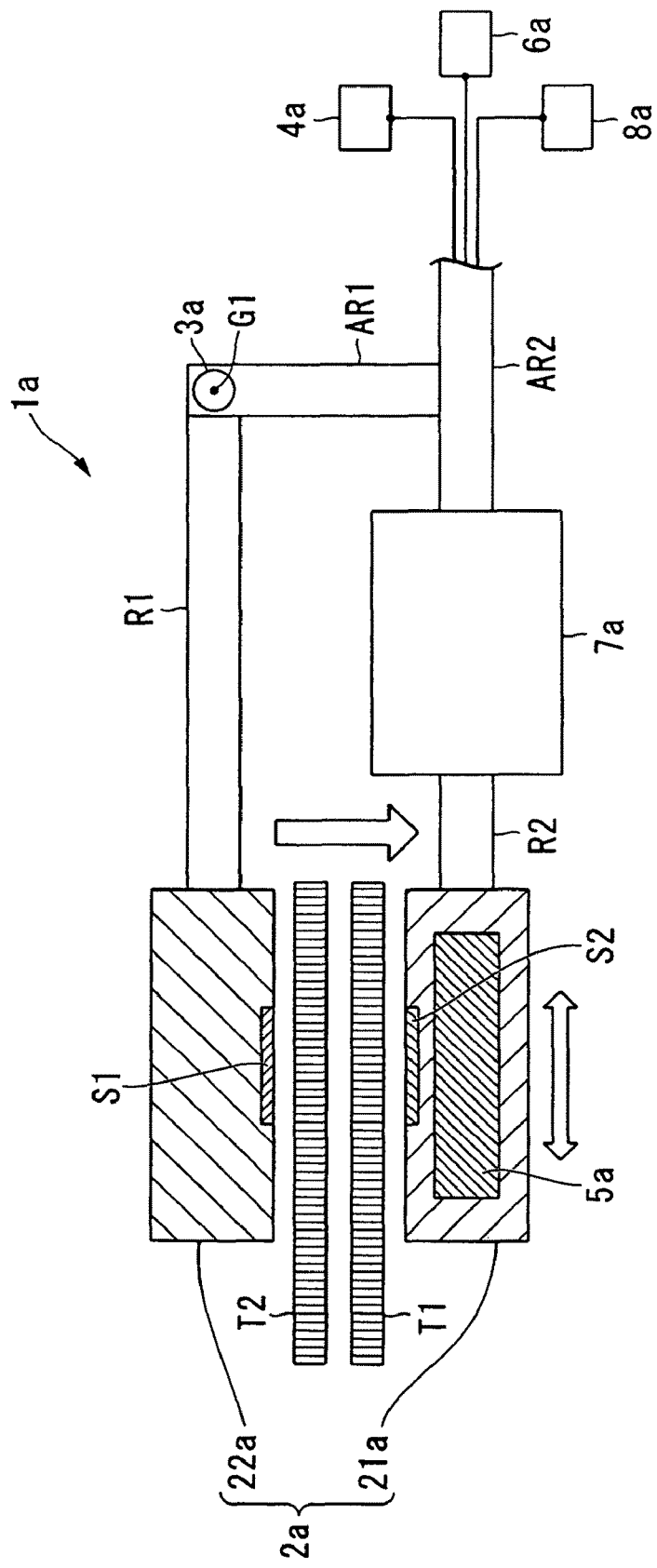
FIG. 1 is a partial cross-sectional schematic diagram showing an embodiment of a first device of the present invention.

EXPLANATION OF REFERENCE NUMERALS 1a, 1b, 1c . . . device
2a, 2b . . . clamping part
3a, 31b, 32b . . . pressing part
3c . . . pressing part (balloon)
4a, 4b, 4c . . . pressure control part
5a, 5b, 5c . . . heating element
6a, 6b, 6c . . . heating control part
7a, 7b, 7c . . . vibration generating part
8a, 8b, 8c . . . vibration control part
T1, T2, T3, T4 . . . adherend (biological tissue or biological tissue bonding material)
B . . . adherend (blood vessel)
ST . . . adherend (stent)

BEST MODE FOR CARRYING OUT THE INVENTION

The biological tissue bonding medical instrument of the present invention will be explained in detail first.

The biological tissue bonding medical instrument according to the present embodiment has on the surface thereof a portion comprising biological tissue bonding material.

The biological tissue bonding material is not particularly limited, so long as it is a material that can be bonded to biological tissue by, in contact with biological tissue, being subjected to a pressure of $9 \times 10^2$ to $1 \times 10^5$ N/m$^2$ (preferably $1 \times 10^4$ to $5 \times 10^4$ N/m$^2$), to a temperature of 60 to 140° C. (preferably 80 to 110° C.) and to vibration of frequency ranging from 1 to 100 kHz (preferably 10 to 60 kHz). Examples of preferred biological tissue bonding materials include, for instance, wet collagen, polyurethane, vinylon, gelatin, and composite materials of the foregoing.

The time required for bonding the biological tissue bonding material with the biological tissue (time during which the above-described pressure, temperature and vibration are applied to the biological tissue bonding material and the biological tissue, brought into contact with each other), ranges ordinarily from 2 to 240 seconds, preferably from 10 to 120 seconds.

The direction along which vibration is imparted to the biological tissue bonding material and the biological tissue is not particularly limited. For instance, the direction of the vibration may be substantially parallel to the contact surface of the biological tissue bonding material and the biological tissue, or may be substantially perpendicular to the contact surface of the biological tissue bonding material and the biological tissue. The amplitude of the vibration imparted to the biological tissue bonding material and the biological tissue is not particularly limited, but ranges ordinarily from 0.1 to 100 μm, preferably from 0.2 to 20 μm.

The biological tissue to which the biological tissue bonding material can be bonded is not particularly limited, and may be, for instance, cardiovascular tissue, digestive tissue, skin tissue, tendinous tissue, ligament tissue, mesenchymal/parenchymal tissue, vascular tissue, metabolic tissue, brain tissue, lymphoid tissue, muscular tissue or the like.

The bonding strength between the biological tissue bonding material and the biological tissue ranges ordinarily from 0.1 to 2 MPa, preferably from 0.5 to 1 MPa.

Provided that it has on the surface thereof a portion comprising a biological tissue bonding material, the medical instrument may be wholly constituted by the biological tissue bonding material, or only partly constituted by the biological tissue bonding material.

Examples of the medical instrument include, for instance, a stent, a stent-graft (covered stent), an artificial blood vessel, an adhesion-preventing film, a wound-covering material, a vascular catheter, a cannula, a monitoring tube, an artificial kidney, an artificial heart-lung, a blood circuit for extracorporeal circulation, an A-V shunt for artificial kidneys, an artificial blood vessel, an artificial heart, an artificial cardic valve, a temporary bypass tube for blood, a blood circuit for artificial dialysis, a blood bag, a disposable circuit for apheresis systems, a dialysis membrane, an artificial liver, a nanoparticle cover material, a biosensor cover material, a percutaneous device, an arteriovenous shunt, a pacemaker, an intravenous hyperalimentation catheter, a heart-wrapping net or the like.

When the medical instrument according to the present embodiment is a stent, the latter can be bonded to the inner wall of blood vessels by using the below-described device 1c shown in FIG. 3.

The biological tissue bonding device of the present invention is explained in detail next with reference to accompanying drawings.

[First Embodiment]

A device 1a according to a first embodiment is a device for bonding adherends T1 and T2, and comprises, as shown in FIG. 1, a clamping part 2a for clamping the adherends T1 and T2 between members 21a and 22a; a pressing part 3a for pressing the member 22a towards the member 21a; a pressure control part 4a for controlling the pressure exerted by the pressing part 3a; a heating element 5a built into the member 21a; a heating control part 6a for controlling heating by the heating element 5a; a vibration generating part 7a for generating microvibration; and a vibration control part 8a for controlling the microvibration generated by the vibration generating part 7a.

The kind of the adherends T1 and T2 is not particularly limited. Thus, the adherends T1 and T2 may be both biological tissue, or one of them may be biological tissue and the other biological tissue bonding material. The adherends T1 and T2 may be biological tissue bonding material itself, or a medical instrument having a portion comprising biological tissue bonding material. Examples of biological tissues, biological tissue bonding materials and medical instruments include those described above.

The thickness of the adherends T1 and T2 (thickness in the direction perpendicular to the contact surface of the adherends T1 and T2) is not particularly limited, but ranges ordinarily from 0.01 to 5 mm, preferably from 0.1 to 1 mm. The device 1a according to the first embodiment is appropriate for bonding relatively thin adherends to each other.

As shown in FIG. 1, the clamping part 2a comprises the members 21a and 22a and clamps the adherends T1 and T2 between the members 21a and 22a. The shape, size and so forth of the members 21a and 22a, as well as the shape, size and so forth of the adherend contact surface of the members 21a and 22a are not particularly limited, provided that the adherends T1 and T2 can be clamped between the members 21a and 22a. The members 21a and 22a may be shaped, for instance, as plates, clips, tweezers or the like. The adherend contact surface of the members 21a and 22a may be, for instance, planar, curved, serrated, or shaped as a pinholder. The material of the members 21a and 22a is not particularly limited provided that it does not adhere to the adherends T1 and T2, and may be, for instance, stainless steel, polyester, cellophane, Teflon, dry collagen, polyvinyl chloride, polyethylene, polypropylene, silk, as well as composite materials of the foregoing.

As shown in FIG. 1, the member 22a is attached to an arm AR1, via a rod R1, in such a manner that the member 22a can pivot around a shaft member G1. The pressing part 3a for pivoting the member 22a is provided on the arm AR1, as shown in FIG. 1. The pressing part 3a has an electric motor, an ultrasonic motor, a piezoelectric element or the like as a power source for pivoting the member 22a. Through pivoting of the member 22a, the member 22a is pressed towards the member 21a. Alternatively, one end of a wire may be connected to the member 22a, and the other end of the wire may be pulled from the outside, to press thereby the member 22a towards the member 21a.

As shown in FIG. 1, a sensor S1 is provided on the adherend contact surface of the member 22a, for detecting the clamping force exerted by the clamping part 2a (i.e. the pressure exerted on the adherends T1 and T2 clamped by the clamping part 2a). The sensor S1 and the pressing part 3a are electrically connected to the pressure control part 4a. On the basis of, for instance, the pressure detected by the sensor S1, the pressure control part 4a controls the pressure exerted by the pressing part 3a in such a manner that the clamping force of the clamping part 2a (i.e. the pressure exerted on the adherends T1 and T2 clamped by the clamping part 2a) ranges from $9 \times 10^2$ to $1 \times 10^5$ N/m$^2$ (preferably from $1 \times 10^4$ to $5 \times 10^4$ N/m$^2$).

The heating element 5a built into the member 21a is not particularly limited, and may be, for instance, an electrical heater, a Peltier element, a magnetic body (in which case a varying magnetic field is irradiated from outside) or the like. As shown in FIG. 1, a sensor S2 is provided on the adherend contact surface of the member 21a, for detecting the temperature of the adherends T1 and T2. The sensor S2 and the heating element 5a are electrically connected to the heating control part 6a. On the basis of, for instance, the temperature detected by the sensor S2, the heating control part 6a controls the heat generated by the heating element 5a in such a manner that the temperature of the adherends T1 and T2 clamped by the clamping part 2a ranges from 60 to 140° C. (preferably from 80 to 110° C.). The sensor S2 detects directly the temperature of the adherend T1, but the heat applied to the adherend T1 is transmitted to the adherend T2, as a result of which the temperature of the adherend T1 is influenced by the temperature of the adherend T2 as well. Hence, the temperature of the adherend T2 can be detected on the basis of, for instance, temperature changes in the adherend T1.

As shown in FIG. 1, the member 21a is attached to the vibration generating part 7a via a rod R2. The vibration generating part 7a is attached to an arm AR2. The vibration generating part 7a comprises, as a source for generating microvibration, a vibrating element such as an ultrasonic oscillator, a micro-motor, a magnetic body (in which case a varying magnetic field is irradiated from outside) or the like. The microvibration generated by the vibration generating part 7a is transmitted to the member 21a via the rod R2, which is a vibration transmitting member. The direction of the vibration applied to the member 21a is not particularly limited. In the present embodiment, the direction of the vibration is substantially parallel to the contact surface of the adherends T1 and T2 (direction denoted by the arrow in FIG. 1). The vibration control part 8a, for controlling the microvibration generated by the vibration generating part 7a, is electrically connected to the vibration generating part 7a. The vibration control part 8a controls the microvibration generated by the vibration generating part 7a in such a manner that the frequency of the microvibration in the adherends T1 and T2 clamped by the clamping part 2a ranges from 1 to 100 kHz (preferably from 10 to 60 kHz). The vibration control part 8a controls also the microvibration generated by the vibration generating part 7a in such a manner that the amplitude of the vibration in the adherends T1 and T2 clamped by the clamping part 2a is smaller than 100 μm, preferably smaller than 20 μm. The lower limit of the amplitude of the microvibration is ordinarily 0.1 μm, preferably 0.2 μm. A small vibrator can be used and no horn need be provided, when the adherends T1 and T2 clamped by the clamping part 2a vibrate with an amplitude smaller than 100 μm. This allows reducing as a result the size of the device 1a.

As shown in FIG. 1, the arm AR1 is fixed to the arm AR2. The arm AR2 is connected to a gripping part (not shown), a catheter (not shown), a guide wire (not shown) or the like.

The device 1a bonds the adherends T1 and T2 as described below.

The clamping part 2a clamps the adherends T1 and T2 in contact with each other. Herein, the clamping force of the clamping part 2a is controlled by the clamping force control part 4a in such a manner that the pressure applied to the adherends T1 and T2 clamped by the clamping part 2a ranges from $9\times10^2$ to $1\times10^5$ N/m$^2$ (preferably, from 1 to $5\times10^4$ N/m$^2$).

The heat generated by the heating element 5a is transmitted to the adherends T1 and T2 via the adherend contact surface of the member 21a. The adherends T1 and T2 are heated as a result. Herein, the heating control part 6a controls the heat generated by the heating element 5a in such a manner that the adherends T1 and T2 clamped by the clamping part 2a are heated at 60 to 140° C. (preferably 80 to 110° C.). The heat generated by the heating element 5a is initially applied to the adherend T1, but since the adherends T1 and T2 are in contact with each other, the heat applied to the adherend T1 is transmitted to the adherend T2, whereupon the adherend T2 becomes heated as well.

The microvibration generated by the vibration generating part 7a is transmitted to the member 21a via the rod R2, which is a vibration transmitting member. Herein, the vibration control part 8a controls the vibration generated by the vibration generating part 7a in such a manner that the adherends T1 and T2 clamped by the clamping part 2a vibrate with a frequency ranging from 1 to 100 kHz (preferably, from 10 to 60 kHz). The microvibration generated by the vibration generating part 7a is initially imparted on the adherend T1, but since the adherends T1 and T2 are in contact with each other, the vibration imparted on the adherend T1 is transmitted to the adherend T2, whereupon the adherend T2 becomes vibrated as well. The direction of the vibration imparted to the adherends T1 and T2 is not particularly limited. In the present embodiment, the direction of the vibration is substantially parallel to the contact surface of the adherends T1 and T2 (direction denoted by the arrow in FIG. 1).

The adherends T1 and T2 clamped by the clamping part 2a are in contact with each other. The adherends T1 and T2 are subjected to a pressure of $9\times10^2$ to $1\times10^5$ N/m$^2$ (preferably $10^4$ to $5\times10^4$ N/m$^2$), to a temperature of 60 to 140° C. (preferably 80 to 110° C.) and to vibration of frequency ranging from 1 to 100 kHz (preferably 10 to 60 kHz). The time during which the adherends T1 and T2 are subjected to the above-described pressure, temperature and vibration ranges ordinarily from 2 to 240 seconds, preferably from 10 to 120 seconds. Thereby, the adherends T1 and T2 become bonded solidly and quickly. When the adherends T1 and T2 are subjected to the above-described pressure, temperature and vibration, the damage inflicted on the first and second adherends is small.

[Second Embodiment]

Figure 2:
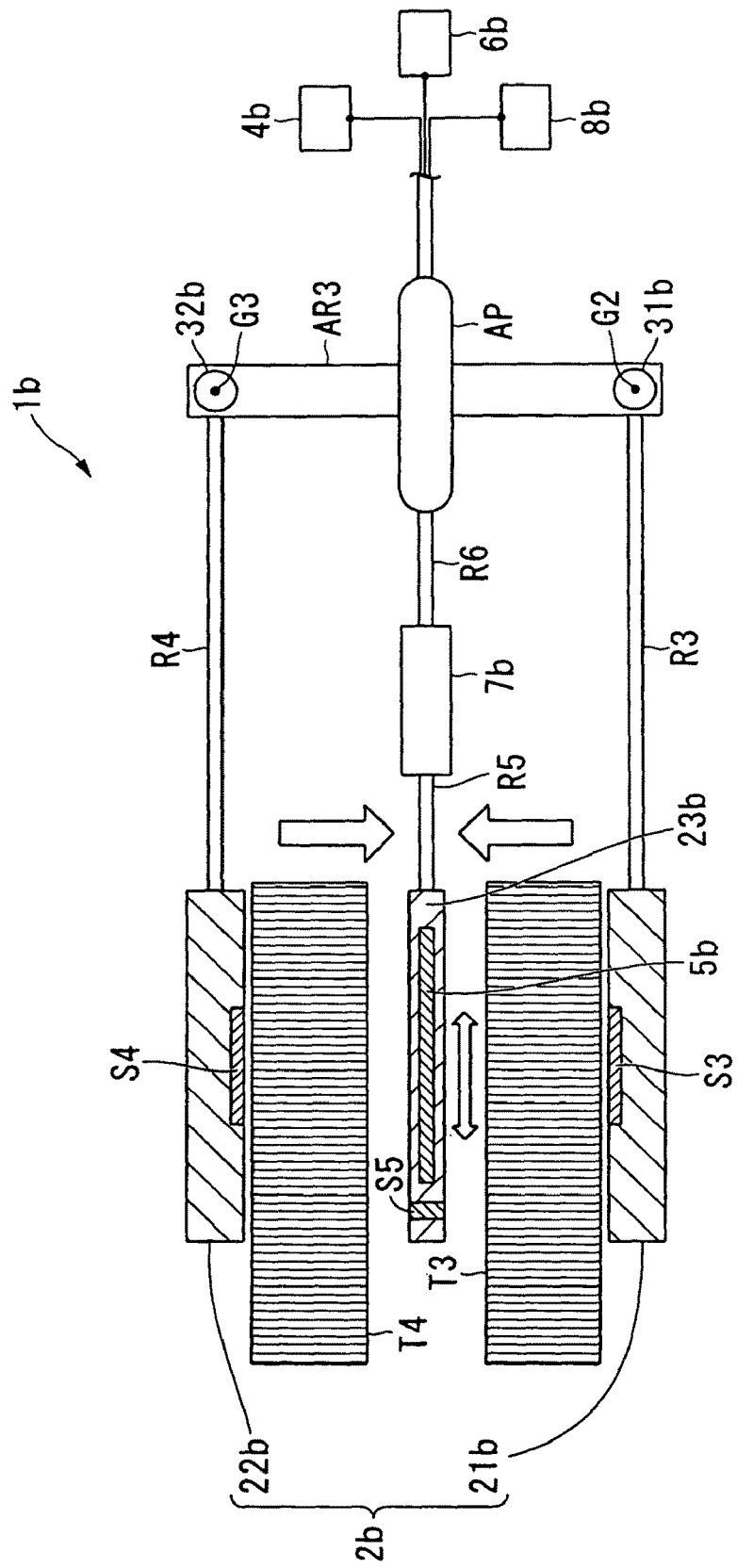
FIG. 2 is a partial cross-sectional schematic diagram showing another embodiment of the first device of the present invention.

A device 1b according to a second embodiment is a device for bonding adherends T3 and T4, and comprises, as shown in FIG. 2, a clamping part 2b for clamping the adherends T3 and T4 between members 21b and 22b; a member 23b interposed between the adherends T3 and T4; a pressing part 31b for pressing the member 21b towards the member 22b; a pressing part 32b for pressing the member 22b towards the member 21b; a pressure control part 4b for controlling the pressure exerted by the pressing parts 31b and 32b; a heating element 5b built into the member 23b; a heating control part 6b for controlling heating by the heating element 5b; a vibration generating part 7b for generating microvibration; and a vibration control part 8b for controlling the microvibration generated by the vibration generating part 7b.

The kind of the adherends T3 and T4 is not particularly limited. Thus, the adherends T3 and T4 may be both biological tissue, or one of them may be biological tissue and the other a biological tissue bonding material. Specific examples of the biological tissue and the biological tissue bonding material are similar to those described above. The thickness of the adherends T3 and T4 (thickness in the direction perpendicular to the contact surface of the adherends T3 and T4) is not particularly limited, but ranges ordinarily from 0.01 to 10 mm, preferably from 0.1 to 5 mm. The device 1b according to the second embodiment is appropriate for bonding relatively thick adherends to each other.

As shown in FIG. 2, the clamping part 2b comprises the members 21b and 22b and clamps the adherends T3 and T4 between the members 21b and 22b. The shape, size and so forth of the members 21b and 22b, as well as the shape, size and so forth of the adherend contact surface of the members 21b and 22b are not particularly limited, provided that the adherends T3 and T4 can be clamped between the members 21b and 22b. The members 21b and 22b may be shaped, for instance, as plates, clips, tweezers or the like. The adherend contact surface of the members 21b and 22b may be, for instance, planar, curved, serrated, or shaped as a pinholder. The shape, size and so forth of the member 23b, as well as the shape, size and so forth of the adherend contact surface of the member 23b are not particularly limited, provided that member 23b can be interposed between the adherends T3 and T4. The member 23b may be shaped, for instance, as a plate, rod or the like. The adherend contact surface of the member 23b may be, for instance, planar, curved, serrated, or shaped as a pinholder. The material of the members 21b, 22b and 23b is not particularly limited provided that it does not adhere to the adherends T3 and T4, and may be, for instance, stainless steel, polyester, cellophane, Teflon, dry collagen, polyvinyl chloride, polyethylene, polypropylene, silk, as well as composite materials of the foregoing.

As shown in FIG. 2, the member 21b is attached to an arm AR3, via a rod R3, in such a manner that the member 21b can pivot around a shaft member G2. The member 22b is attached to the arm AR3, via a rod R4, in such a manner that the member 22b can pivot around a shaft member G3. As shown in FIG. 2, on the arm AR3 there are provided a pressing part 31b for pivoting the member 21b, and a pressing part 32b for pivoting the member 22b. The pressing parts 31b and 32b have each an electric motor, an ultrasonic motor, a piezoelectric element or the like as a power sources for pivoting the members 21b and 22b, respectively. The pressing part 31b causes the member 21b to pivot, to press thereby the member 21b towards the member 22b. The pressing part 32b causes the member 22b to pivot, to press thereby the member 22b towards the member 21b. Alternatively, one end of a wire may be connected to the member 21b, and the other end of the wire may be pulled from the outside, to press thereby the member 21b towards the member 22b. Likewise, one end of a wire may be connected to the member 22b, and the other end of the wire may be pulled from the outside, to press thereby the member 22b towards the member 21b.

As shown in FIG. 2, sensors S3 and S4 are respectively provided on the adherend contact surfaces of the members 21b and 22b, for detecting the clamping force exerted by the clamping part 2b (i.e. the pressure exerted on the adherends T3 and T4 clamped by the clamping part 2b). The sensors S3 and S4 and the pressing parts 31b and 32b are electrically connected to the pressure control part 4b. On the basis of, for instance, the pressure detection by the sensors S3 and S4, the pressure control part 4b controls the pressure exerted by the pressing parts 31b and 32b in such a manner that the clamping force of the clamping part 2b (i.e. the pressure exerted on the adherends T3 and T4 clamped by the clamping part 2b) ranges from $9\times10^2$ to $1\times10^5$ N/m$^2$ (preferably from $1\times10^4$ to $5\times10^4$ N/m$^2$). The pressure control part 4b controls ordinarily the pressure exerted by the pressing parts 31b and 32b in such a manner so as to equalize the pressure exerted by the pressing part 31b on the member 21b, towards the member 22b, with the pressure exerted by the pressing part 32b on the member 22b, towards the member 21b.

The heating element 5b built into the member 23b is not particularly limited, and may be, for instance, an electrical heater, a Peltier element, a magnetic body (in which case a varying magnetic field is irradiated from outside) or the like. A sensor S5 for detecting the temperature of the adherends T3 and T4 is provided on the adherend contact surface of the member 23b. The sensor S5 and the heating element 5b are electrically connected to the heating control part 6b. On the basis of, for instance, the temperature detected by the sensor S5, the heating control part 6b controls the heat generated by the heating element 5b in such a manner that the temperature of the adherends T3 and T4 clamped by the clamping part 2b ranges from 60 to 140° C. (preferably from 80 to 110° C.).

As shown in FIG. 2, the member 23b is attached to the vibration generating part 7b via a rod R5. The vibration generating part 7b is attached to an adapter AP via a rod R6. The adapter AP is attached to the arm AR3. The vibration generating part 7b comprises, as a source for generating microvibration, a vibrating element such as an ultrasonic oscillator, a micro-motor, a magnetic body (in which case a varying magnetic field is irradiated from outside) or the like. The microvibration generated by the vibration generating part 7b is transmitted to the member 23b via the rod R5, which is a vibration transmitting member. The direction of the vibration applied to the member 23b is not particularly limited. In the present embodiment, the direction of the vibration is substantially parallel to the contact surface of the adherends T3 and T4 (direction denoted by the arrow in FIG. 2). The vibration control part 8b, for controlling the microvibration generated by the vibration generating part 7b, is electrically connected to the vibration generating part 7b. The vibration control part 8b controls the microvibration generated by the vibration generating part 7b in such a manner that the frequency of the microvibration in the adherends T3 and T4 clamped by the clamping part 2b ranges from 1 to 100 kHz (preferably from 10 to 60 kHz). The vibration control part 8b controls also the microvibration generated by the vibration generating part 7b in such a manner that the amplitude of the vibration in the adherends T3 and T4 clamped by the clamping part 2b is smaller than 100 μm, preferably smaller than 20 μm. The lower limit of the amplitude of the microvibration is ordinarily 0.1 μm, preferably 0.2 μm. A small vibrator can be used and no horn need be provided, when the adherends T3 and T4 clamped by the clamping part 2b vibrate with an amplitude smaller than 100 μm. This allows reducing as a result the size of the device 1b. The microvibration generated by the vibration generating part 7b is transmitted to the adapter AP via the rod R6. However, the adapter AP has a mechanism (for instance, a microvibration absorbing mechanism using an elastic member) that allows absorbing microvibration, so that the microvibration is not transmitted to the arm AR3. The adapter AP is connected to a gripping part (not shown), a catheter (not shown), a guide wire (not shown) or the like.

The device 1b bonds the adherends T3 and T4 as described below.

The clamping part 2b clamps the adherends T3 and T4, with the latter in contact with each other, and with the member 23b interposed between, and in contact with, the adherends T3 and T4. Herein, the clamping force of the clamping part 2b is controlled by the clamping force control part 4b in such a manner that the pressure applied to the adherends T3 and T4 clamped by the clamping part 2b ranges from $9\times10^2$ to $1\times10^5$ N/m$^2$ (preferably, from $1\times10^4$ to $5\times10^4$ N/m$^2$).

The heat generated by the heating element 5b is transmitted to the adherends T3 and T4 via the adherend contact surface of the member 23b. The adherends T3 and T4 are heated as a result. Herein, the heating control part 6b controls the heat generated by the heating element 5b in such a manner that the adherends T3 and T4 clamped by the clamping part 2b are heated at 60 to 140° C. (preferably 80 to 110° C.).

The microvibration generated by the vibration generating part 7b is transmitted to the member 23b via the rod R5, which is a vibration transmitting member. Since the member 23b is interposed between the adherends T3 and T4, the vibration of the member 23b is transmitted to the adherends T3 and T4. Herein, the vibration control part 8b controls the vibration generated by the vibration generating part 7b in such a manner that the adherends T3 and T4 clamped by the clamping part 2b vibrate with a frequency ranging from 1 to 100 kHz (preferably, from 10 to 60 kHz). The direction of the vibration imparted to the adherends T3 and T4 is not particularly limited. In the present embodiment, the direction of the vibration is substantially parallel to the contact surface of the adherends T3 and T4 (direction denoted by the arrow in FIG. 2).

The adherends T3 and T4 clamped by the clamping part 2b are in contact with each other. The adherends T3 and T4 are subjected to a pressure of $9\times10^2$ to $1\times10^5$ N/m$^2$ (preferably $1\times10^4$ to $5\times10^4$ N/m$^2$), to a temperature of 60 to 140° C. (preferably 80 to 110° C.) and to vibration of frequency ranging from 1 to 100 kHz (preferably 10 to 60 kHz). The time during which the adherends T3 and T4 are subjected to the above-described pressure, temperature and vibration, ranges ordinarily from 2 to 240 seconds, preferably from 10 to 120 seconds. Thereby, the adherends T3 and T4 become bonded solidly and quickly. When the adherends T3 and T4 are subjected to the above-described pressure, temperature and vibration, the damage inflicted on the adherends T3 and T4 is small. The portions of the adherends T3 and T4 that do not come into contact, by being interposed the member 23b between them, do not become bonded.

[Third Embodiment]

A device 1c according to a third embodiment is a device for bonding a stent ST, which is inserted into a blood vessel B, to the inner wall of the blood vessel B. As shown in FIG. 3, the device 1c comprises a member 24c having a built-in heating element 5c; a balloon 3c for pressing the member 24c towards the inner wall of the blood vessel B; a pressure control part 4c for controlling the pressure exerted by the balloon 3c; a heating control part 6c for controlling heating by the heating element 5c; a vibration generating part 7c for generating microvibration; and a vibration control part 8c for controlling the microvibration generated by the vibration generating part 7c.

The shape, size and so forth of the member 24c, as well as the shape, size and so forth of the stent contact surface of the member 24c are not particularly limited, provided that the member 24c can be inserted into the stent ST. The member 24c may be shaped, for instance, as a plate, rod or the like. The stent contact surface of the member 24c may be, for instance, planar, curved, serrated, or shaped as a pinholder. The material of the member 24c is not particularly limited, provided that it does not adhere to the stent ST, and may be, for instance, stainless steel, polyester, Teflon, polyvinyl chloride, polyethylene, polypropylene, silk, aramid resin, polyether ether ketone resin, silicone resin, polycarbonate resin, as well as composite materials of the foregoing.

The surface of the stent ST is coated with biological tissue bonding material such as wet collagen, polyurethane, vinylon, gelatin, and composite materials of the foregoing.

Figure 3:
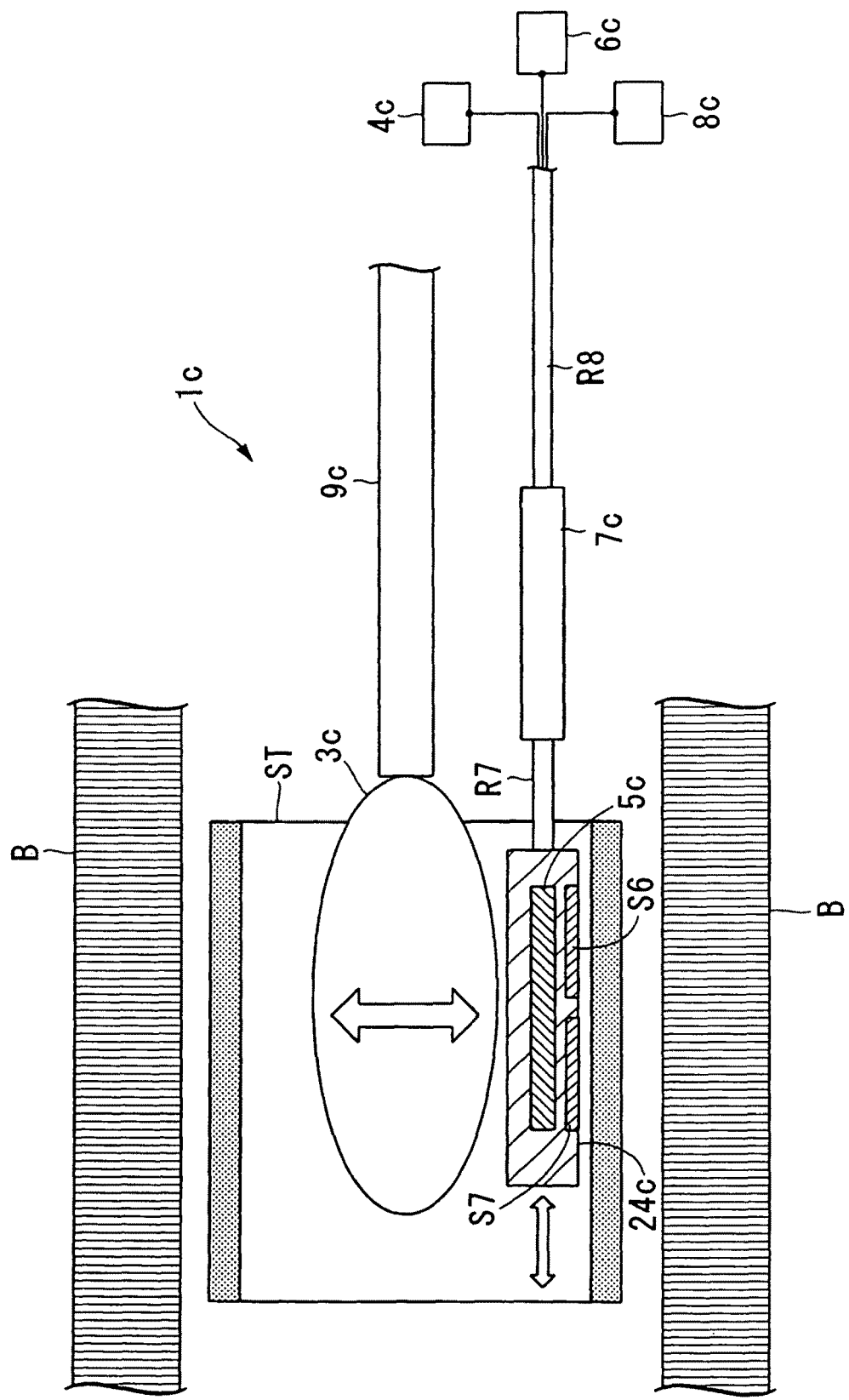
FIG. 3 is a partial cross-sectional schematic diagram showing an embodiment of a second device of the present invention.

As illustrated in FIG. 3, the balloon 3c passes through a balloon catheter 9c. A fluid is pressurized into the balloon 3c, via the balloon catheter 9c, to inflate the balloon 3c and dilate thereby a stenotic part of the blood vessel B while pressing the member 24c towards the inner wall of the blood vessel B. A sensor S6 for detecting the pressure exerted on the stent ST and the blood vessel B is provided on the stent contact surface of the member 24c. The sensor S6 and the device (not shown) that pressurizes fluid into the balloon 3 are electrically connected to the pressure control part 4c. On the basis of, for instance, the pressure detected by the sensor S6, the pressure control part 4c controls the pressure exerted by the balloon 3c in such a manner that the pressure exerted on the stent ST and the blood vessel B ranges from $9 \times 10^2$ to $1 \times 10^5$ N/m² (preferably from $1 \times 10^4$ to $5 \times 10^4$ N/m²).

The heating element 5c built into the member 24c is not particularly limited, and may be, for instance, an electrical heater, a Peltier element, a magnetic body (in which case a varying magnetic field is irradiated from outside) or the like. As shown in FIG. 3, a sensor S7, for detecting the temperature of the stent ST and the inner wall of the blood vessel B, is provided on the stent contact surface of the member 24c. The sensor S7 and the heating element 5c are electrically connected to the heating control part 6c. On the basis of, for instance, the temperature detected by the sensor S7, the heating control part 6c controls the heat generated by the heating element 5c in such a manner that the temperature of the stent ST and the inner wall of the blood vessel B ranges from 60 to 140° C. (preferably from 80 to 110° C.). The sensor S7 detects directly the temperature of the stent ST. However, the heat applied to the stent ST is transmitted to the inner wall of the blood vessel B, as a result of which the temperature of the stent ST is influenced by the temperature of the inner wall of the blood vessel B. Hence, the temperature of the inner wall of the blood vessel B can be detected on the basis of, for instance, temperature changes in the stent ST.

As shown in FIG. 3, the member 24c is attached to the vibration generating part 7c via a rod R7. The vibration generating part 7c is attached to a rod R8. The vibration generating part 7c comprises, as a source for generating microvibration, a vibrating element such as an ultrasonic oscillator, a micro-motor, a magnetic body (in which case a varying magnetic field is irradiated from outside) or the like. The microvibration generated by the vibration generating part 7c is transmitted to the member 24c via the rod R7, which is a vibration transmitting member. The direction of the vibration applied to the member 24c is not particularly limited. In the present embodiment, the direction of the vibration is substantially parallel to the contact surface of the stent ST and the inner wall of the blood vessel B (direction denoted by the arrow in FIG. 3). The vibration control part 8c, for controlling the microvibration generated by the vibration generating part 7c, is electrically connected to the vibration generating part 7c. The vibration control part 8c controls the vibration generated by the vibration generating part 7c in such a manner that the frequency of the microvibration in the stent ST and the inner wall of the blood vessel B ranges from 1 to 100 kHz (preferably from 10 to 60 kHz). The vibration control part 8c controls also the microvibration generated by the vibration generating part 7c in such a manner that the amplitude of the vibration in the stent ST and the inner wall of the blood vessel B is smaller than 100 µm, preferably smaller than 20 µm. The lower limit of the amplitude of the microvibration is ordinarily 0.1 µm, preferably 0.2 µm. A small vibrator can be used and no horn need be provided, when the stent ST and the inner wall of the blood vessel B vibrate with an amplitude smaller than 100 µm. This allows reducing as a result the size of the device 1c. The rod R8 is connected to a gripping part (not shown), a catheter (not shown), a guide wire (not shown) or the like.

The device 1c bonds the stent ST and the inner wall of the blood vessel B as described below.

When fluid is pressurized into the balloon 3c, via the balloon catheter 9c, the balloon 3c inflates, thereby dilating a stenotic segment of the blood vessel B while pressing the member 24c towards the inner wall of the blood vessel B. The stent ST is pressed thereby against the inner wall of the blood vessel B. As a result, the stent ST is brought into contact with the inner wall of the blood vessel B. Herein, the pressure control part 4c controls the pressure exerted by the balloon 3c in such a manner that the pressure exerted on the stent ST and the inner wall of the blood vessel B ranges from $9 \times 10^2$ to $1 \times 10^5$ N/m² (preferably, from $1 \times 10^4$ to $5 \times 10^4$ N/m²).

The heat generated by the heating element 5c is transmitted to the stent ST and the inner wall of the blood vessel B via the stent contact surface of the member 24c. The stent ST and the inner wall of the blood vessel B are heated as a result. Herein, the heating control part 6c controls the heat generated by the heating element 5c in such a manner that the stent ST and the inner wall of the blood vessel B are heated at 60 to 140° C. (preferably 80 to 110° C.). The heat generated by the heating element 5c is initially applied to the stent ST, but since the stent ST and the inner wall of the blood vessel B are in contact with each other, the heat applied to the stent ST is transmitted to the inner wall of the blood vessel B, whereupon the inner wall of the blood vessel B becomes heated as well.

The microvibration generated by the vibration generating part 7c is transmitted to the member 24c via the rod R7, which is a vibration transmitting member, and is transmitted from the member 24c to the stent ST and the inner wall of the blood vessel B. Herein, the vibration control part 8c controls the vibration generated by the vibration generating part 7c in such a manner that the stent ST and the inner wall of the blood vessel B vibrate with a frequency ranging from 1 to 100 kHz (preferably, from 10 to 60 kHz). The microvibration generated by the vibration generating part 7c is initially applied to the stent ST, but since the stent ST and the inner wall of the blood vessel B are in contact with each other, the vibration applied to the stent ST is transmitted to the inner wall of the blood vessel B to cause the blood vessel B to vibrate as well. The direction of the vibration imparted to the stent ST and the inner wall of the blood vessel B is not particularly limited. In the present embodiment, the direction of the vibration is substantially parallel to the contact surface of the stent ST and the inner wall of the blood vessel B (direction denoted by the arrow in FIG. 3).

With the stent ST and the inner wall of the blood vessel B thus in contact with each other, the stent ST and the inner wall of the blood vessel B are subjected to a pressure of $9 \times 10^2$ to $1 \times 10^5$ N/m$^2$ (preferably $1 \times 10^4$ to $5 \times 10^4$ N/m$^2$), to a temperature of 60 to 140° C. (preferably 80 to 110° C.) and to vibration of frequency ranging from 1 to 100 kHz (preferably 10 to 60 kHz). The time during which the stent ST and the inner wall of the blood vessel B are subjected to the above-described pressure, temperature and vibration, ranges ordinarily from 2 to 240 seconds, preferably from 10 to 120 seconds. Thereby, the stent ST and the inner wall of the blood vessel B become bonded solidly and quickly. When the stent ST and the inner wall of the blood vessel B are subjected to the above-described pressure, temperature and vibration, the damage inflicted on the stent ST and the inner wall of the blood vessel B is small.

EXAMPLES

Experimental Example 1

The purpose of the present experimental example is to identify the conditions that are required for bonding biological tissues together.

Method 1 (ultrasonic scalpel): Two blood vessel tissue slices (luminal surface of porcine aorta) were brought into contact with each other, a predetermined frequency (kHz), amplitude (μm), temperature (° C.), pressure-bonding time (seconds) and pressure (N/m$^2$) were applied to the two blood vessel tissue slices by using a commercially available ultrasonic scalpel (Sonopet, made by Miwatec Co., Ltd.), thus bonding of the two blood vessel tissue slices was tried.

Method 2 (thermocompression bonding): Two blood vessel tissue slices (luminal surface of porcine aorta) were stacked on a temperature-controlled heated plate. A predetermined pressure (N/m$^2$) was applied to the two blood vessel tissue slices, thus bonding of the two blood vessel tissue slices was tried.

Method 3 (thermocompression bonding+microvibration): Two blood vessel tissue slices (luminal surface of porcine aorta) were stacked on a temperature-controlled heated plate. A predetermined frequency (kHz), amplitude (μm), temperature (° C.), pressure-bonding time (seconds) and pressure (N/m$^2$) were applied to the two blood vessel tissue slices, thus bonding of the two blood vessel tissue slices was tried.

The specific conditions and results of the various methods are summarized in Table 1.

TABLE 1

| Method | Frequency (kHz) | Amplitude (μm) | Temperature (° C.) | Pressure-bonding time (sec) | Pressure (N/m$^2$) | Bonding strength (MPa) |
|---|---|---|---|---|---|---|
| 1 (Ultrasonic scalpel) | 25 | 30-180 | 50-55 | 1-2 | 20000-25000 | Bonding failed |
| 1 (Ultrasonic scalpel) | 25 | 30-180 | 60-90 | 3-4 | 20000-25000 | 0.01-0.17 |
| 1 (Ultrasonic scalpel) | 25 | 30-180 | 120-150 | 6-7 | 20000-25000 | Tissue damege |
| 2 (Thermocompression bonding) | — | — | 60-140 | 5-10 | 20000-25000 | Bonding failed |
| 3 (Thermocompression bonding + microvibration) | 7 | 4-9 | 100-120 | 10-240 | 20000-60000 | 0-0.2 |
| 3 (Thermocompression bonding + microvibration) | 12 | 4-9 | 100-120 | 10-240 | 20000-60000 | 1.0-1.8 |
| 3 (Thermocompression bonding + microvibration) | 14.5 | 4-9 | 100-120 | 10-240 | 20000-60000 | 0.1-1.0 |

As shown in Table 1, the blood vessel tissue slices could be bonded together within a short time (3 to 4 seconds) in method 1. When the bonding time was too short (1 to 2 seconds), however, the blood vessel tissue slices failed to bond to each other, while an excessively long bonding time (6 to 7 seconds) resulted in bonded tissue damage (carbonization due to heating). The bonding strength between the blood vessel tissue slices was at most 0.17 MPa, so that the tissue slices could be easily detached from each other by hand pulling.

As shown in Table 1, the blood vessel tissue slices failed to bond to each other in method 2. Presumably, that is because bonding between biological tissues requires factors (vibration) other than heat and pressure.

As shown in Table 1, the blood vessel tissue slices could be bonded together in method 3. Although the temperature required in method 3 is similar to that of method 1, the pressure bonding time and the pressure required in method 3 were greater than those in method 1, while the amplitude required in method 3 was smaller than that of method 1. The bonding strength obtained in method 3 was greater than that of method 1, of about ten-fold the bonding strength obtained by method 1, in particular, for a frequency of 12 kHz, such that the tissue slices could not be readily detached by hand pulling.

Experimental Example 2

The purpose of the present experimental example was to search for materials capable of bonding with biological tissue under the conditions identified in Experimental example 1.

Blood vessel tissue slices (luminal surface of porcine aorta) were brought into contact with various materials, followed by application of vibration, with 25 kHz frequency and 80 μm amplitude, a temperature of 100° C., and a pressure of $5 \times 10^4$ N/m$^2$, over 1 to 5 seconds.

Figure 4:
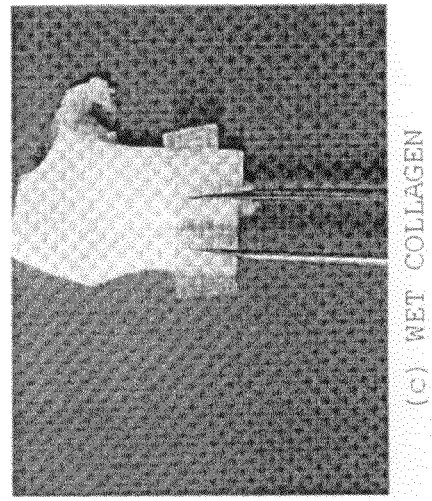
FIG. 4 is a set of pictures showing the solidly bonded state between a blood vessel tissue slice and (a) polyurethane, (b) vinylon, or (c) wet collagen.
Figure 4:
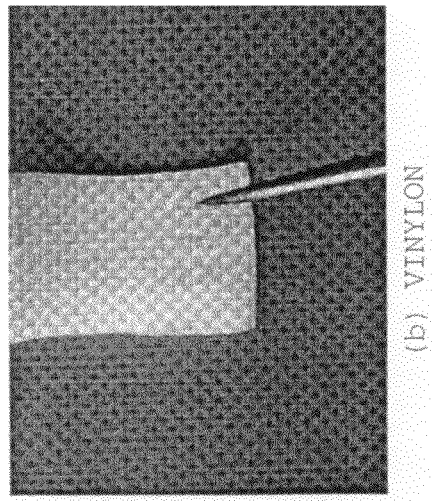
Figure 4:
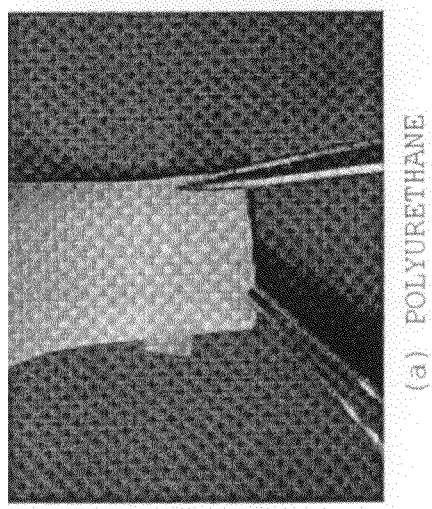

The results (see FIG. 4) showed that wet collagen (obtained by cross-linking type-1 collagen, made by Koken Co., Ltd., with glutaraldehyde), polyurethane (ESPA, made by Toyobo Co., Ltd.), vinylon (Vinylon, made by Kuraray Co., Ltd.), and gelatin (obtained by cross-linking purified gelatin, made by Wako Pure Chemical Industries, Ltd., with glutaraldehyde)

bonded solidly to blood vessel tissue slices. Nylon (nylon net, made by Gunze Sangyo) bonded to the blood vessel tissue slices, but insufficiently. Polyester (Ube graft, made by Ube Medical Inc.), stainless steel (SUS364, commercialized product), cellophane (cellophane film, made by Tokyo Cellophane Co., Ltd.), dry collagen (obtained by cross-linking type-1 collagen, made by Koken Co., Ltd., with glutaraldehyde, followed by drying), and Teflon (Gore-Tex EPTFE graft, made by Japan Gore-Tex Co., Ltd.) failed to bond to the blood vessel tissue slices. A tensile measurement was carried out after bonding. A bonding strength below 0.2 MPa was judged as "insufficient bonding", while a bonding strength of 0.2 MPa or greater was judged as "solid bonding".

Figure 5:
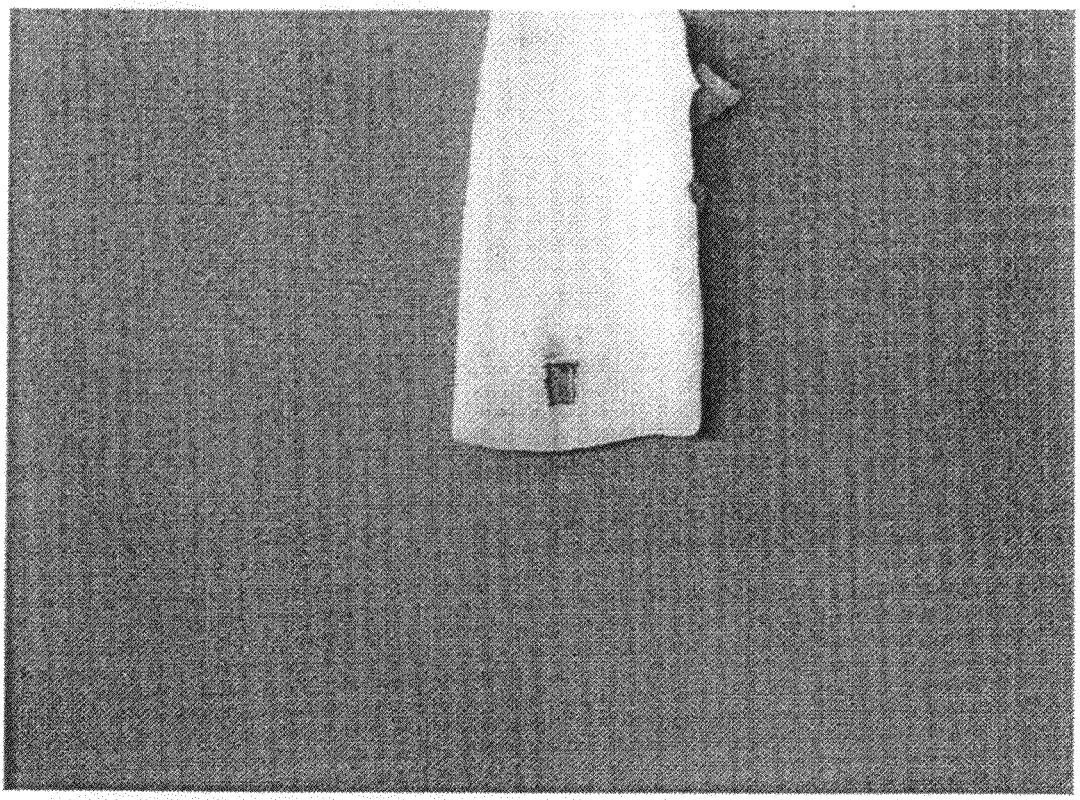
FIG. 5 is a picture showing a polyurethane-coated stainless steel piece bonded to a blood vessel tissue slice.
Figure 6:
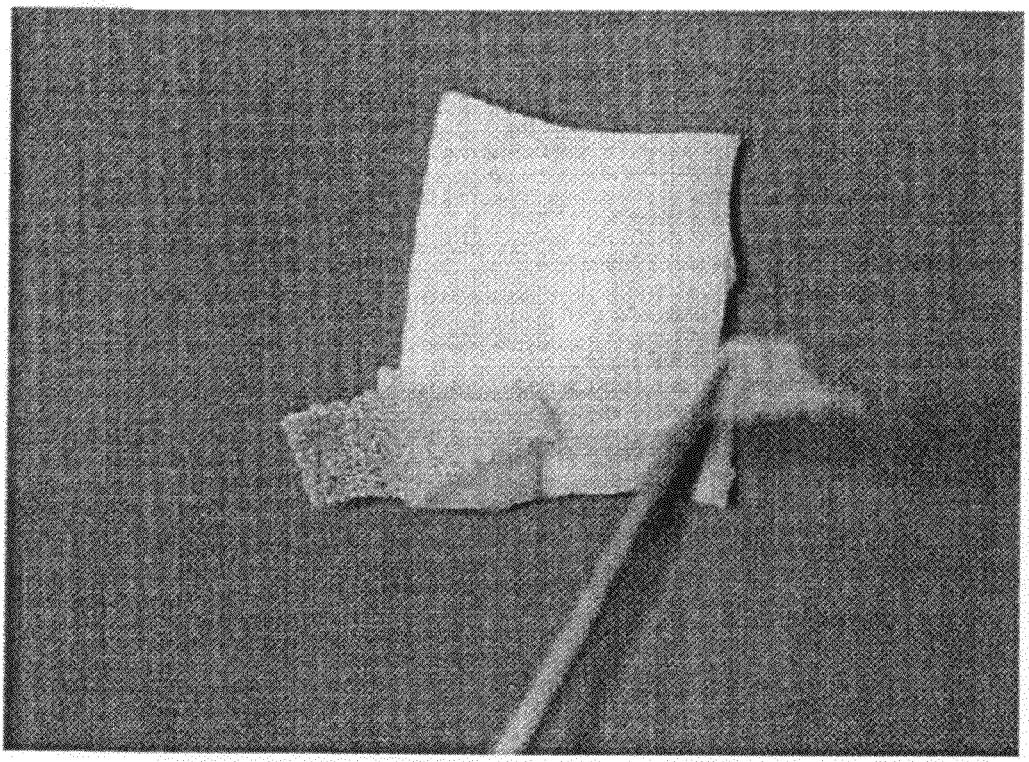
FIG. 6 is a picture showing a polyurethane-coated polyester piece bonded to a blood vessel tissue slice.

Experiments were carried out, under the same conditions as above, for bonding a polyurethane-coated stainless steel piece (FIG. 5) and a polyurethane-coated polyester piece (FIG. 6) to blood vessel tissue slices.

INDUSTRIAL APPLICABILITY

The present invention is useful for solidly bonding biological tissue (for instance, blood vessels or the like) to biological tissue or to a biological tissue bonding material.

The invention claimed is:

1. A device for bonding biological tissue, as a first adherend, and biological tissue or a biological tissue bonding material, as a second adherend,
the device comprising:
a clamping part clamping the first and second adherends in such a manner that the first and second adherends are in contact with each other;
a clamping force control part controlling the clamping force of the clamping part in such a manner that the pressure exerted on the first and second adherends clamped by the clamping part is $9 \times 10^2$ to $1 \times 10^5$ N/m$^2$;
a heating part heating the first and/or second adherend clamped by the clamping part;
a heating control part controlling the heating by the heating part in such a manner that the temperature of the first and second adherends clamped by the clamping part is 60 to 140° C.;
a vibration part imparting vibration to the first and/or second adherend clamped by the clamping part, wherein a direction of the vibration is substantially parallel to a contact surface of the adherend; and
a vibration control part controlling the vibration imparted by the vibration part in such a manner that the first and second adherends clamped by the clamping part vibrate with a frequency of 1 to 100 kHz.

2. The device according to claim 1, wherein the vibration control part controls the vibration imparted by the vibration part in such a manner that the first and second adherends clamped by the clamping part vibrate with an amplitude smaller than 100 μm.

3. The device according to claim 1, wherein
the clamping part clamps the first and second adherends between a first contact part that is in contact with the first adherend and a second contact part that is in contact with the second adherend;
the heating part heats the first and/or second adherend clamped by the clamping part by heating the first and/or second contact part; and
the vibration part imparts vibration to the first and/or second adherend clamped by the clamping part by imparting vibration to the first and/or second contact part.

4. The device according to claim 1, comprising an interposing part that can be interposed between the first and second adherends, with the first and second adherend in contact with each other, wherein
the heating part heats the first and/or second adherend clamped by the clamping part by heating the interposing part; and
the vibration part imparts vibration to the first and/or second adherend clamped by the clamping part by imparting vibration to the interposing part.

5. A device for bonding biological tissue, as a first adherend, and biological tissue or a biological bonding material, as a second adherend,
the device comprising:
a pressing part pressing one of the first and second adherends towards the other one of the adherends;
a pressure control part controlling the pressure by the pressing part in such a manner that the pressure exerted on the first and second adherends is $9 \times 10^2$ to $1 \times 10^5$ N/m$^2$;
a heating part heating the first and/or second adherend;
a heating control part controlling the heating by the heating part in such a manner that the temperature of the first and second adherends is 60 to 140° C.;
a vibration part imparting vibration to the first and/or second adherend, wherein a direction of the vibration is substantially parallel to a contact surface of the adherend; and
a vibration control part controlling the vibration imparted by the vibration part in such a manner that the first and second adherends vibrate with a frequency of 1 to 100 kHz.

6. The device according to claim 5, wherein the vibration control part controls the vibration imparted by the vibration part in such a manner that the first and second adherends vibrate with an amplitude smaller than 100 μm.

7. The device according to claim 5, comprising a contact part that is in contact with the first or second adherend, wherein
the heating part heats the first or second adherend by heating the contact part; and
the vibration part imparts vibration to the first or second adherend by imparting vibration to the contact part.

8. The device according to claim 7, wherein the pressing part presses one of the first and second adherends towards the other one of the adherends by pressing the contact part towards one of the first and second adherends.

9. A device for bonding biological tissue, as a first adherend, and biological tissue or a biological tissue bonding material, as a second adherend,
the device comprising:
a clamping part configured to clamp the first and second adherends in such a manner that the first and second adherends are in contact with each other;
a clamping force control part configured to control the clamping force of the clamping part and the pressure exerted on the first and second adherends clamped by the clamping part is $9 \times 10^2$ to $1 \times 10^5$ N/m$^2$;
a heating part configured to control the first and/or second adherend clamped by the clamping part;
a heating control part configured to control the heating by the heating part and a temperature of the first and second adherends clamped by the clamping part is 60 to 140° C.;
a vibration part configured to impart vibration to the first and/or second adherend clamped by the clamping part, a direction of the vibration being substantially parallel to a contact surface of the adherend; and a vibration control part configured to control the vibration imparted by the vibration part where the first and second adherends clamped by the clamping part vibrate with a frequency of 1 to 100 kHz.

10. The device according to claim 9, wherein the vibration control part is configured to control the vibration to the first and second adherends clamped by the clamping part at an amplitude smaller than 100 μm.

11. The device according to claim 9, wherein
the clamping part is configured to clamp the first and second adherends between a first contact part that is in contact with the first adherend and a second contact part that is in contact with the second adherend;
the heating part is configured to heat the first and/or second adherend clamped by the clamping part by heating the first and/or second contact part; and
the vibration part is configured to impart vibration to the first and/or second adherend clamped by the clamping part by imparting vibration to the first and/or second contact part.

12. The device according to claim 9, further comprising an interposing part interposed between the first and second adherends, with the first and second adherend in contact with each other, wherein
the heating part is configured to heat the first and/or second adherend clamped by the clamping part by heating the interposing part; and
the vibration part is configured to impart vibration to the first and/or second adherend clamped by the clamping part by imparting vibration to the interposing part.

13. A device for bonding biological tissue, as a first adherend, and biological tissue or a biological bonding material, as a second adherend,
the device comprising:
a pressing part configured to press one of the first and second adherends towards the other one of the adherends;
a pressure control part configured to control the pressure by the pressing part and the pressure exerted on the first and second adherends is $9 \times 10^2$ to $1 \times 10^5$ N/m$^2$;
a heating part configured to heat the first and/or second adherend;
a heating control part configured to control the heating by the heating part in such a manner that the temperature of the first and second adherends is 60 to 140° C.;
a vibration part configured to impart vibration to the first and/or second adherend, a direction of the vibration being substantially parallel to a contact surface of the adherend; and
a vibration control part configured to control the vibration imparted by the vibration part in such a manner that the first and second adherends vibrate with a frequency of 1 to 100 kHz.

14. The device according to claim 13, wherein the vibration control part is configured to control the vibration to the first and second adherends clamped by the clamping part at an amplitude smaller than 100 μm.

15. The device according to claim 13, comprising a contact part that is in contact with the first or second adherend, wherein
the heating part is configured to heat the first or second adherend by heating the contact part; and
the vibration part is configured to impart vibration to the first or second adherend by imparting vibration to the contact part.

16. The device according to claim 15, wherein the pressing part is configured to press one of the first and second adherends towards the other one of the adherends by pressing the contact part towards one of the first and second adherends.

* * * * *